US010384041B2

(12) United States Patent
Patel et al.

(10) Patent No.: US 10,384,041 B2
(45) Date of Patent: *Aug. 20, 2019

(54) SELF CONTAINED WOUND DRESSING APPARATUS

(71) Applicant: Smith & Nephew, Inc., Memphis, TN (US)

(72) Inventors: Harish A. Patel, Norfolk, MA (US); Dianne Acheson, Norwood, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/484,622

(22) Filed: Apr. 11, 2017

(65) Prior Publication Data

US 2017/0259047 A1   Sep. 14, 2017

Related U.S. Application Data

(63) Continuation of application No. 13/866,346, filed on Apr. 19, 2013, now Pat. No. 9,629,986, which is a
(Continued)

(51) Int. Cl.
*A61M 35/00* (2006.01)
*A61M 1/00* (2006.01)
(Continued)

(52) U.S. Cl.
CPC ....... *A61M 27/00* (2013.01); *A61F 13/00063* (2013.01); *A61F 13/00068* (2013.01);
(Continued)

(58) Field of Classification Search
CPC ........ A61M 35/00; A61M 1/00; A61M 27/00; A61F 13/00; A61F 13/02
See application file for complete search history.

(56) References Cited

U.S. PATENT DOCUMENTS 3,367,332 A   2/1968   Groves
3,520,300 A   7/1970   Flower, Jr.
(Continued)

FOREIGN PATENT DOCUMENTS

DE            198 44 355      4/2000
DE       20 2004 017 052      7/2005
(Continued)

OTHER PUBLICATIONS

European Examination Report, re EP Application No. 06803097.2, dated May 8, 2012.
(Continued)

*Primary Examiner* — Tatyana Zalukaeva
*Assistant Examiner* — Ilya Y Treyger
(74) *Attorney, Agent, or Firm* — Knobbe, Martens, Olson & Bear, LLP (57) ABSTRACT

The composite wound dressing apparatus promotes healing of a wound via the use of a vacuum pump. The vacuum pump applies a vacuum pressure to the wound to effectively draw wound fluid or exudate away from the wound bed. The vacuum pump is tethered to the wound dressing and is portable, preferably, carried by the patient in a support bag, which permits patient mobility. Moreover, the patient does not need to be constrained for any period of time while exudate is being removed from the wound.

16 Claims, 4 Drawing Sheets

Related U.S. Application Data continuation of application No. 12/879,715, filed on Sep. 10, 2010, now Pat. No. 8,444,612, which is a continuation of application No. 11/516,216, filed on Sep. 6, 2006, now abandoned.

(60) Provisional application No. 60/714,912, filed on Sep. 7, 2005.

(51) Int. Cl.
    *A61M 27/00*     (2006.01)
    *A61F 13/00*     (2006.01)
    *A61F 13/02*     (2006.01)

(52) U.S. Cl.
CPC .......... *A61M 1/009* (2014.02); *A61M 1/0031* (2013.01); *A61M 1/0066* (2013.01); *A61M 1/0072* (2014.02); *A61M 1/0088* (2013.01); *A61F 2013/0054* (2013.01); *A61F 2013/0074* (2013.01); *A61F 2013/0091* (2013.01); *A61F 2013/00174* (2013.01); *A61F 2013/00412* (2013.01); *A61F 2013/00536* (2013.01); *A61F 2013/00748* (2013.01); *A61M 1/0096* (2014.02); *A61M 2205/15* (2013.01); *A61M 2205/3344* (2013.01); *A61M 2205/8206* (2013.01); *A61M 2209/08* (2013.01); *A61M 2209/088* (2013.01)

(56) References Cited

U.S. PATENT DOCUMENTS

| | | |
|---|---|---|
| 3,874,387 A | 4/1975 | Barbieri |
| 3,972,328 A | 8/1976 | Chen |
| 4,224,941 A | 9/1980 | Stivala |
| 4,398,910 A | 8/1983 | Blake et al. |
| 4,624,656 A | 11/1986 | Clark et al. |
| 4,664,662 A | 5/1987 | Webster |
| 4,681,562 A | 7/1987 | Beck et al. |
| 4,710,165 A | 12/1987 | McNeil et al. |
| 4,969,880 A | 11/1990 | Zamierowski |
| 5,055,195 A | 10/1991 | Trasch et al. |
| 5,055,198 A | 10/1991 | Shettigar |
| 5,056,510 A | 10/1991 | Gilman |
| 5,060,642 A | 10/1991 | Gilman |
| 5,086,763 A | 2/1992 | Hathman |
| 5,100,396 A | 3/1992 | Zamierowski |
| 5,106,629 A | 4/1992 | Cartmell et al. |
| 5,141,503 A | 8/1992 | Sewell, Jr. |
| 5,152,757 A | 10/1992 | Eriksson |
| 5,176,663 A | 1/1993 | Svedman et al. |
| 5,181,905 A | 1/1993 | Flam |
| 5,238,732 A | 8/1993 | Krishnan |
| 5,261,893 A | 11/1993 | Zamierowski |
| 5,527,293 A | 6/1996 | Zamierowski |
| 5,549,584 A | 8/1996 | Gross |
| 5,636,643 A | 6/1997 | Argenta et al. |
| 5,643,189 A | 7/1997 | Masini |
| 5,645,081 A | 7/1997 | Argenta et al. |
| 5,678,564 A | 10/1997 | Lawrence et al. |
| 5,701,917 A | 12/1997 | Khouri |
| 5,707,499 A | 1/1998 | Joshi et al. |
| 5,733,337 A | 3/1998 | Carr et al. |
| 5,759,570 A | 6/1998 | Arnold |
| 5,779,657 A | 7/1998 | Daneshvar |
| 5,833,646 A | 11/1998 | Masini |
| 5,911,222 A | 6/1999 | Lawrence et al. |
| 6,071,267 A | 6/2000 | Zamierowski |
| 6,117,111 A | 9/2000 | Fleischmann |
| 6,135,116 A | 10/2000 | Vogel et al. |
| 6,142,982 A | 11/2000 | Hunt et al. |
| 6,168,800 B1 | 1/2001 | Dobos et al. |
| 6,174,306 B1 | 1/2001 | Fleischmann |
| 6,183,438 B1 | 2/2001 | Berguer |
| 6,225,523 B1 | 5/2001 | Masini |
| 6,261,276 B1 | 7/2001 | Reitsma |
| 6,261,283 B1 | 7/2001 | Morgan et al. |
| 6,287,521 B1 | 9/2001 | Quay et al. |
| 6,345,623 B1 | 2/2002 | Heaton et al. |
| 6,398,767 B1 | 6/2002 | Fleischmann |
| 6,442,413 B1 | 8/2002 | Silver |
| 6,458,109 B1 | 10/2002 | Henley et al. |
| 6,488,643 B1 | 12/2002 | Tumey et al. |
| 6,520,982 B1 | 2/2003 | Boynton et al. |
| 6,553,998 B2 | 4/2003 | Heaton et al. |
| 6,557,704 B1 | 5/2003 | Randolph |
| 6,599,262 B1 | 7/2003 | Masini |
| 6,607,495 B1 | 8/2003 | Skalak et al. |
| 6,626,891 B2 | 9/2003 | Ohmstede |
| 6,648,862 B2 | 11/2003 | Watson |
| 6,681,003 B2 | 1/2004 | Linder et al. |
| 6,685,681 B2 | 2/2004 | Lockwood et al. |
| 6,695,823 B1 | 2/2004 | Lina et al. |
| 6,695,824 B2 | 2/2004 | Howard et al. |
| 6,752,794 B2 | 6/2004 | Lockwood et al. |
| 6,755,807 B2 | 6/2004 | Risk, Jr. et al. |
| 6,764,462 B2 | 7/2004 | Risk, Jr. et al. |
| 6,767,334 B1 | 7/2004 | Randolph |
| 6,787,682 B2 | 9/2004 | Gilman |
| 6,794,554 B2 | 9/2004 | Sessions et al. |
| 6,800,074 B2 | 10/2004 | Henley et al. |
| 6,814,079 B2 | 11/2004 | Heaton et al. |
| 6,824,533 B2 | 11/2004 | Risk, Jr. et al. |
| 6,855,135 B2 | 2/2005 | Lockwood et al. |
| 6,855,860 B2 | 2/2005 | Ruszczak et al. |
| 6,856,821 B2 | 2/2005 | Johnson |
| 6,936,037 B2 | 8/2005 | Bubb et al. |
| 6,942,633 B2 | 9/2005 | Odland |
| 6,942,634 B2 | 9/2005 | Odland |
| 6,951,553 B2 | 10/2005 | Bubb et al. |
| 7,022,113 B2 | 4/2006 | Lockwood et al. |
| 7,067,709 B2 | 6/2006 | Murate et al. |
| 7,077,832 B2 | 7/2006 | Fleischmann |
| 7,087,806 B2 | 8/2006 | Scheinberg et al. |
| 7,108,683 B2 | 9/2006 | Zamierowski |
| 7,117,869 B2 | 10/2006 | Heaton et al. |
| 7,128,735 B2 | 10/2006 | Weston |
| 7,216,651 B2 | 5/2007 | Argenta et al. |
| 7,279,612 B1 | 10/2007 | Heaton et al. |
| 7,361,184 B2 | 4/2008 | Joshi |
| 7,381,859 B2 | 6/2008 | Hunt et al. |
| 7,524,315 B2 | 4/2009 | Blott et al. |
| 7,553,306 B1 | 6/2009 | Hunt et al. |
| 7,569,742 B2 | 8/2009 | Haggstrom et al. |
| 7,611,500 B1 | 11/2009 | Lina et al. |
| 7,615,036 B2 | 11/2009 | Joshi et al. |
| 7,625,362 B2 | 12/2009 | Boehringer et al. |
| 7,645,253 B2 | 1/2010 | Gura et al. |
| 7,699,823 B2 | 4/2010 | Haggstrom et al. |
| 7,708,724 B2 | 5/2010 | Weston |
| 7,775,998 B2 | 8/2010 | Riesinger |
| 7,776,028 B2 | 8/2010 | Miller et al. |
| 7,779,625 B2 | 8/2010 | Joshi et al. |
| 7,811,269 B2 | 10/2010 | Boynton et al. |
| 7,838,717 B2 | 11/2010 | Haggstrom et al. |
| 7,846,141 B2 | 12/2010 | Weston |
| 7,896,864 B2 | 3/2011 | Lockwood et al. |
| 7,909,805 B2 | 3/2011 | Weston |
| 7,910,791 B2 | 3/2011 | Coffey |
| 7,922,676 B2 | 4/2011 | Daskal et al. |
| 7,922,703 B2 | 4/2011 | Riesinger |
| 7,942,866 B2 | 5/2011 | Radl et al. |
| 7,959,624 B2 | 6/2011 | Riesinger |
| 7,964,766 B2 | 6/2011 | Blott et al. |
| 7,976,519 B2 | 7/2011 | Bubb et al. |
| 8,062,272 B2 | 11/2011 | Weston |
| 8,062,273 B2 | 11/2011 | Weston |
| 8,080,702 B2 | 12/2011 | Blott et al. |
| 8,092,441 B2 | 1/2012 | Sugito |
| 8,100,887 B2 | 1/2012 | Weston et al. |
| 8,118,794 B2 | 2/2012 | Weston |
| 8,207,392 B2 | 6/2012 | Haggstrom et al. |
| 8,212,100 B2 | 7/2012 | Moore |

(56) References Cited

U.S. PATENT DOCUMENTS

| | | |
|---|---|---|
| 8,282,611 B2 | 10/2012 | Weston |
| 8,303,552 B2 | 11/2012 | Weston |
| 8,444,612 B2 | 5/2013 | Patel et al. |
| 8,460,255 B2 | 6/2013 | Joshi et al. |
| 8,529,548 B2 | 9/2013 | Blott et al. |
| 8,545,464 B2 | 10/2013 | Weston |
| 8,569,566 B2 | 10/2013 | Blott et al. |
| 8,628,505 B2 | 1/2014 | Weston |
| 8,829,263 B2 | 9/2014 | Haggstrom et al. |
| 9,168,330 B2 | 10/2015 | Joshi et al. |
| 9,669,138 B2 | 6/2017 | Joshi et al. |
| 9,795,725 B2 | 10/2017 | Joshi et al. |
| 2001/0031943 A1 | 10/2001 | Urie |
| 2001/0043943 A1 | 11/2001 | Coffey |
| 2001/0051781 A1 | 12/2001 | Augustine et al. |
| 2002/0065494 A1 | 5/2002 | Lockwood et al. |
| 2002/0115952 A1 | 8/2002 | Johnson et al. |
| 2002/0128578 A1 | 9/2002 | Johnson |
| 2002/0128804 A1 | 9/2002 | Geva |
| 2002/0135336 A1 | 9/2002 | Zhou et al. |
| 2002/0143286 A1 | 10/2002 | Tumey |
| 2002/0161346 A1 | 10/2002 | Lockwood et al. |
| 2003/0009244 A1 | 1/2003 | Engleson et al. |
| 2003/0040687 A1 | 2/2003 | Boynton et al. |
| 2003/0078532 A1 | 4/2003 | Ruszczak et al. |
| 2003/0093041 A1 | 5/2003 | Risk, Jr. et al. |
| 2003/0097100 A1 | 5/2003 | Watson |
| 2003/0105649 A1 | 6/2003 | Sheiner et al. |
| 2003/0208149 A1 | 11/2003 | Coffey |
| 2003/0212357 A1 | 11/2003 | Pace |
| 2003/0212359 A1 | 11/2003 | Butler |
| 2003/0219469 A1 | 11/2003 | Johnson et al. |
| 2004/0006319 A1 | 1/2004 | Lina |
| 2004/0019464 A1 | 1/2004 | Martucci et al. |
| 2004/0030304 A1 | 2/2004 | Hunt |
| 2004/0039415 A1 | 2/2004 | Zamierowski |
| 2004/0054338 A1 | 3/2004 | Bybordi |
| 2004/0054775 A1 | 3/2004 | Poliac et al. |
| 2004/0064111 A1 | 4/2004 | Lockwood et al. |
| 2004/0064132 A1 | 4/2004 | Boehringer et al. |
| 2004/0073151 A1 | 4/2004 | Weston |
| 2004/0078223 A1 | 4/2004 | Sacco et al. |
| 2004/0087884 A1 | 5/2004 | Haddock et al. |
| 2004/0093026 A1 | 5/2004 | Weidenhagen et al. |
| 2004/0143458 A1 | 7/2004 | Pulkkinen |
| 2004/0167482 A1 | 8/2004 | Watson |
| 2004/0193218 A1 | 9/2004 | Butler |
| 2004/0241213 A1 | 12/2004 | Bray |
| 2004/0243073 A1 | 12/2004 | Lockwood et al. |
| 2004/0249353 A1 | 12/2004 | Risk, Jr. et al. |
| 2004/0260230 A1 | 12/2004 | Randolph |
| 2005/0004534 A1 | 1/2005 | Lockwood et al. |
| 2005/0010153 A1 | 1/2005 | Lockwood et al. |
| 2005/0012616 A1 | 1/2005 | Forster et al. |
| 2005/0020955 A1 | 1/2005 | Sanders et al. |
| 2005/0033124 A1 | 2/2005 | Kelly et al. |
| 2005/0058694 A1 | 3/2005 | Nielsen |
| 2005/0065471 A1 | 3/2005 | Kuntz |
| 2005/0070835 A1 | 3/2005 | Joshi |
| 2005/0070858 A1 | 3/2005 | Lockwood et al. |
| 2005/0085795 A1 | 4/2005 | Lockwood et al. |
| 2005/0090787 A1 | 4/2005 | Risk, Jr. et al. |
| 2005/0114176 A1 | 5/2005 | Dominick et al. |
| 2005/0119737 A1 | 6/2005 | Bene et al. |
| 2005/0131327 A1 | 6/2005 | Lockwood et al. |
| 2005/0137539 A1 | 6/2005 | Biggie et al. |
| 2005/0147562 A1 | 7/2005 | Hunter et al. |
| 2005/0222528 A1 | 10/2005 | Weston |
| 2005/0240111 A1 | 10/2005 | Chung |
| 2006/0029650 A1 | 2/2006 | Coffey |
| 2006/0069365 A1 | 3/2006 | Sperl et al. |
| 2006/0107642 A1 | 5/2006 | Smith et al. |
| 2006/0155260 A1 | 7/2006 | Blott et al. |
| 2006/0213527 A1 | 9/2006 | Argenta et al. |
| 2006/0224051 A1 | 10/2006 | Teller et al. |
| 2006/0225787 A1 | 10/2006 | Newrones et al. |
| 2006/0228057 A1 | 10/2006 | Newrones et al. |
| 2006/0246922 A1 | 11/2006 | Gasbarro et al. |
| 2006/0259102 A1 | 11/2006 | Slatkine |
| 2007/0055209 A1 | 3/2007 | Patel et al. |
| 2007/0128055 A1 | 6/2007 | Lee |
| 2007/0179460 A1 | 8/2007 | Adahan |
| 2007/0225663 A1 | 9/2007 | Watt et al. |
| 2008/0009681 A1 | 1/2008 | Hussiny |
| 2008/0051716 A1 | 2/2008 | Stutz |
| 2008/0306456 A1 | 12/2008 | Riesinger |
| 2009/0012484 A1 | 1/2009 | Nielsen et al. |
| 2010/0160880 A1 | 6/2010 | Weston |
| 2011/0009835 A1 | 1/2011 | Blott |
| 2011/0028918 A1 | 2/2011 | Hartwell |
| 2011/0054421 A1 | 3/2011 | Hartwell |
| 2011/0087178 A2 | 4/2011 | Weston |
| 2011/0118683 A1 | 5/2011 | Weston |
| 2011/0172615 A2 | 7/2011 | Greener |
| 2012/0157942 A1 | 6/2012 | Weston |
| 2013/0267921 A1 | 10/2013 | Weston |
| 2013/0274688 A1 | 10/2013 | Weston |
| 2013/0331822 A1 | 12/2013 | Patel |
| 2015/0065965 A1 | 3/2015 | Haggstrom |
| 2016/0058927 A1 | 3/2016 | Weston |
| 2018/0028729 A1 | 2/2018 | Joshi et al. |

FOREIGN PATENT DOCUMENTS

| | | |
|---|---|---|
| EP | 0 512 543 | 11/1992 |
| EP | 0 853 950 | 7/1998 |
| EP | 1 088 569 | 4/2001 |
| EP | 1 219 311 | 7/2002 |
| EP | 1 922 044 | 4/2011 |
| EP | 2 021 046 | 3/2012 |
| EP | 2 603 699 | 6/2013 |
| EP | 1 684 146 | 7/2014 |
| EP | 3 072 542 | 9/2016 |
| EP | 3 062 751 | 8/2017 |
| EP | 3 257 486 | 12/2017 |
| FR | 1163907 | 10/1958 |
| FR | 2 939 320 | 6/2010 |
| GB | 2 307 180 A | 11/1996 |
| GB | 2 329 127 A | 3/1999 |
| GB | 2 336 546 A | 10/1999 |
| GB | 2 307 180 B | 6/2000 |
| GB | 2 344 531 A | 6/2000 |
| GB | 2 415 908 | 1/2006 |
| GB | 2511523 | 9/2014 |
| JP | H04-354722 | 12/1992 |
| KR | 2002-0032508 | 5/2002 |
| RU | 131622 | 8/2013 |
| WO | WO 1991/01706 | 2/1991 |
| WO | WO 1993/009727 | 5/1993 |
| WO | WO 1993/19710 | 10/1993 |
| WO | WO 1994/20041 | 9/1994 |
| WO | WO 1996/05873 | 2/1996 |
| WO | WO 2000/21586 | 4/2000 |
| WO | WO 2001/037922 | 5/2001 |
| WO | WO 2003/005943 | 1/2003 |
| WO | WO 2003/018098 | 3/2003 |
| WO | WO 2003/030966 | 4/2003 |
| WO | WO 2003/045492 | 6/2003 |
| WO | WO 2003/057070 | 7/2003 |
| WO | WO 2003/057071 | 7/2003 |
| WO | WO 2003/057307 | 7/2003 |
| WO | WO 2003/086232 | 10/2003 |
| WO | WO 2003/092620 | 11/2003 |
| WO | WO 2003/094090 | 11/2003 |
| WO | WO 2003/101508 | 12/2003 |
| WO | WO 2004/018020 | 3/2004 |
| WO | WO 2004/071279 | 8/2004 |
| WO | WO 2005/009488 | 2/2005 |
| WO | WO 2005/025447 | 3/2005 |
| WO | WO 2005/109297 | 11/2005 |
| WO | WO 2005/115497 | 12/2005 |
| WO | WO 2005/123170 | 12/2005 |

(56) References Cited

FOREIGN PATENT DOCUMENTS

| WO | WO 2007/030599 | 3/2007 |
|---|---|---|
| WO | WO 2009/066104 | 5/2009 |
| WO | WO 2009/124125 | 10/2009 |

OTHER PUBLICATIONS

European Examination Report, re EP Application No. 06803097.2, dated Nov. 3, 2011.
European Examination Report, re EP Application No. 14200239.3, dated May 6, 2015.
KCI, "V.A.C. Freedom User's Guide", May 2002, in 16 pages.
KCI Licensing, Inc., "V.A.C Drape Instructions for Use", Oct. 2003, in 2 pages.
Kendall ULTEC Hydrocolloid Dressing (4"x4"), product ordering page, web page downloaded Jul. 13, 2014.
Notice of Opposition—Statement of Facts and Evidence re EP 2 708 216 dated Jan. 5, 2017, in 18 pages.
Membrane Filters, in 17 pages, from website: http://www.advantecmfs.com/catalog/filt/membrane.pdf#page=11 (date unknown, but believed to be copyright 2001-2011).
Protz, Kerstin: "Modern Wundauflagen unterstutzen Heilungsprozess", Wundversorgung: Indikation and Anwendung, Geriatrie Journal Apr. 2005, pp. 3333-3339.
Brief Communications and Accompanying Filed Items, re European Patent No. 2 708 216, dated Apr. 11, 2018, in 48 pages.
International Search Report and Written Opinion, re PCT Application No. PCT/US2006034825, dated Apr. 16, 2007.
International Preliminary Report on Patentability, re PCT Application No. PCT/US2006/034825, dated Mar. 11, 2008.
Interlocutory Decision in Opposition and Accompanying Items, re European Patent No. 2 708 216, dated Jun. 27, 2018, in 29 pages.
Nullification of the German part of European patent 2 021 046 (German file references 60 2007 021 330.4), dated Nov. 23, 2015, with translation.
Provision of the Minutes, re European Patent No. 2 708 216, dated Jun. 27, 2018, in 5 pages.
Written Submission in Preparation to Oral Proceedings and Accompanying Filed Items, re European Patent No. 2 708 216, dated Apr. 5, 2018, in 42 pages.
Written Submission in Preparation to Oral Proceedings and Accompanying Items, re European Patent No. 2 708 216, filed Apr. 6, 2018 (dated Apr. 5, 2018), in 178 pages.
Written Submission in Preparation to Oral Proceedings and Accompanying Items, re European Patent No. 2 708 216, dated Apr. 19, 2018, in 64 pages.
Written Submission in Preparation to Oral Proceedings and Accompanying Items, re European Patent No. 2 708 216, dated Jun. 5, 2018, in 77 pages.
Annex to the Summons, re European Patent No. EP 2 708 216, dated Oct. 30, 2017, in 6 pages.
Reply of the Patent Proprietor to the Notice of Opposition, re European Patent No. EP 2 708 216, dated Jun. 20, 2017, in 4 pages.
Main request during Opposition procedure, re European Patent No. EP 2 708 216, dated Jun. 20, 2017, in 2 pages.
Amended Claims with Annotations, re European Patent No. EP 2 708 216, dated Jun. 20, 2017, in 2 pages.
Notice of Appeal and subsequently filed items, re European U.S. Pat. No. 2 708 216, dated Aug. 13, 2018, in 4 pages.
Reply to Appeal and subsequently filed items, re European U.S. Pat. No. 2 708 216, dated Mar. 8, 2019, in 116 pages.
Statement of Grounds of Appeal and subsequently filed items, re EP 2 708 216, dated Oct. 23, 2018, in 260 pages.

SELF CONTAINED WOUND DRESSING APPARATUS

CROSS-REFERENCE TO RELATED APPLICATIONS

This application is a continuation of U.S. patent application Ser. No. 13/866,346, filed on Apr. 19, 2013, now U.S. Pat. No. 9,629,986, which is a continuation of U.S. patent application Ser. No. 12/879,715, filed Sep. 10, 2010, now U.S. Pat. No. 8,444,612, which is a continuation of U.S. patent application Ser. No. 11/516,216 filed on Sep. 6, 2006, which claims priority to U.S. Provisional Patent Application Ser. No. 60/714,912, filed on Sep. 7, 2005. The priority of these prior applications is expressly claimed and their disclosures are hereby incorporated by reference in their entirety.

BACKGROUND

Technical Field

The present disclosure relates to an apparatus for treating an open wound, and, more specifically, relates to a self-contained wound dressing with a portable pump system which draws wound fluids into a collection canister supported by the patient.

Description of Related Art

Wound closure involves the migration of epithelial and subcutaneous tissue adjacent the wound towards the center of the wound until the wound closes. Unfortunately, closure is difficult with large wounds or wounds that have become infected. In such wounds, a zone of stasis (i.e. an area in which localized swelling of tissue restricts the flow of blood to the tissues) forms near the surface of the wound. Without sufficient blood flow, the epithelial and subcutaneous tissues surrounding the wound not only receive diminished oxygen and nutrients, but, are also less able to successfully fight microbial infection and, thus, are less able to close the wound naturally. Such wounds have presented difficulties to medical personnel for many years.

Wound dressings have been used in the medical industry to protect and/or facilitate healing of open wounds. One popular technique has been to use negative pressure therapy, which is also known as suction or vacuum therapy. A variety of negative pressure devices have been developed to allow excess wound fluids, i.e., exudates to be removed while at the same time isolating the wound to protect the wound and, consequently, effect recovery time. Various wound dressings have been modified to promote the healing of open wounds.

Issues that continually need to be addressed when using a wound dressing include ease of use, efficiency of healing a wound, portability and negative pressure control capabilities. Thus, there remains a need to constantly improve negative pressure wound dressings for open wounds.

SUMMARY

In accordance with a preferred embodiment, a wound dressing apparatus includes a wound dressing member dimensioned for positioning relative to a wound bed, a portable vacuum pump in fluid communication with the wound dressing member for applying subatmospheric pressure to facilitate removal of fluid from the wound dressing member, and being be carried by the body of a patient, and a collection canister carried by the body of the patient and in fluid communication with the vacuum pump for collecting fluids removed from the wound dressing member. Preferably, the vacuum source includes a peristaltic vacuum pump and is adapted to produce subatmospheric pressure ranging between about 20 mmHg and about 500 mmHg, more preferably, about 75 mmHg to about 125 mmHg. The collection canister may include an absorbent material to contain the fluid removed from the wound dressing member. Preferably, the apparatus also include a body support bag which is adapted for mounting to the patient. The body support bag may have a pouch for retaining at least one of the collection canister and vacuum pump.

The vacuum pump preferably includes control means to control operation thereof. A pressure sensor may be incorporated with the control means to detect pressure at a predetermined location relative to the wound dressing member, and send a corresponding signal to the control means. The control means may include a controller adapted to control or vary the output of the vacuum source. The vacuum pump preferably includes a self-contained battery.

The preferred wound dressing member includes a lower member positionable adjacent the wound bed, an upper absorbent member positionable adjacent the lower member, and a top member. The upper absorbent member comprises a material selected from the group consisting of foams, nonwoven composite fabrics, cellulosic fabrics, super absorbent polymers, and combinations thereof. The upper absorbent member may also include at least one of a medicament, an anti-infective agent, an antimicrobial, polyhexamethylene biguanide (hereinafter, "PHMB"), antibiotics, debridement agents, analgesics, healing factors, vitamins, growth factors and nutrients.

In another preferred embodiment, a wound dressing apparatus, includes a wound dressing member dimensioned for positioning relative to a wound bed, a portable vacuum pump in fluid communication with the wound dressing member for applying subatmospheric pressure to facilitate removal of fluid from the wound dressing member, and having a self contained battery for operating the vacuum pump, a collection canister in fluid communication with the vacuum pump for collecting fluids removed from the wound dressing member and a body support bag attachable to the body of the patient and having a pouch for retaining at least one of the collection canister and the vacuum pump.

A method for facilitating healing of a wound is also disclosed. The method includes the steps of positioning a wound dressing member relative to a wound bed, introducing a portable vacuum pump to be in fluid communication with the wound dressing member for applying subatmospheric pressure to facilitate removal of fluid from the wound dressing member, connecting a collection canister in fluid communication with the vacuum pump for collecting fluids removed from the wound dressing member, mounting a body support bag having a retaining pouch and positioning at least one of the collection canister and the vacuum pump into the retaining pouch of the body support bag.

BRIEF DESCRIPTION OF THE DRAWINGS

Various embodiments of the subject wound dressing are described herein with reference to the drawings wherein.

DETAILED DESCRIPTION OF PREFERRED EMBODIMENTS

The composite wound dressing apparatus of the present disclosure promotes healing of a wound via the use of an external peristaltic vacuum pump. The external peristaltic pump applies a vacuum pressure to the wound to effectively draw wound fluid or exudate away from the wound bed. The external peristaltic pump is tethered to the wound dressing and is portable, preferably, carried by the patient, which permits patient mobility. Moreover, the patient does not need to be constrained for any period of time during therapy and while exudates is being removed from the wound.

Figure 1:
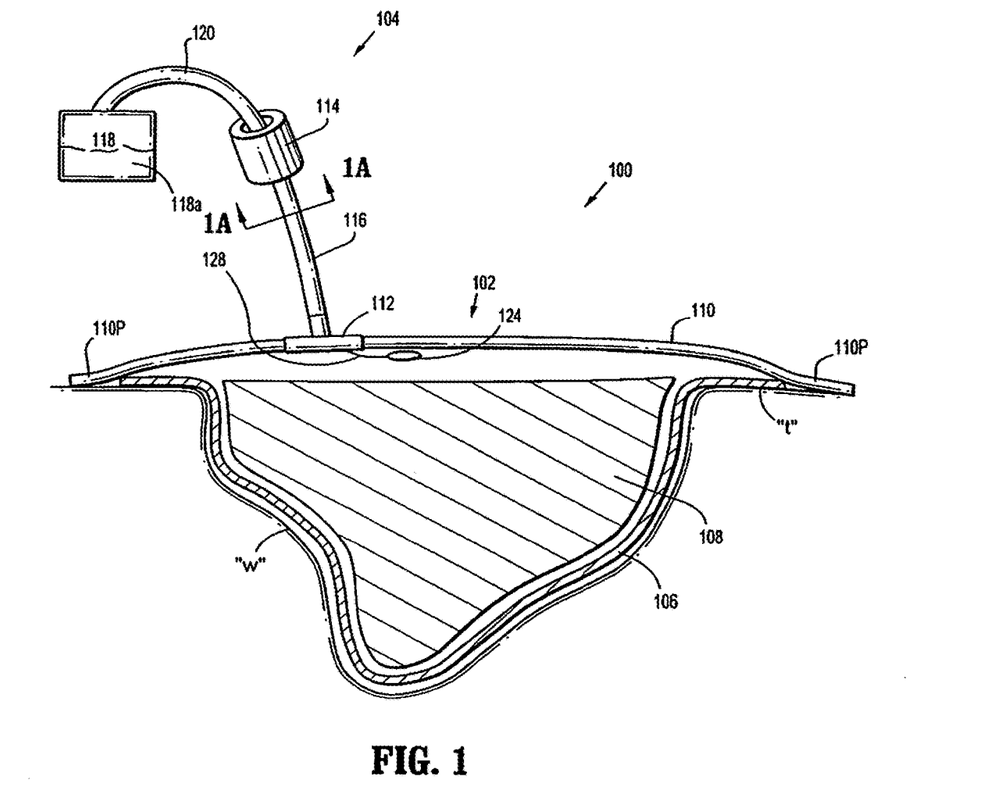
FIG. 1 is a partial cross-sectional view of a self contained wound dressing apparatus in accordance with the principles of the present disclosure illustrating the wound dressing member, pump system and collection canister.

Referring now to FIG. 1, the wound dressing apparatus 100 in accordance with a preferred embodiment of the present disclosure is illustrated. Wound dressing apparatus 100 includes composite wound dressing 102 and pump system 104 tethered to the wound dressing 102. Wound dressing 102 is in the form of an article with multiple layers arranged in juxtaposed or superposed relation. The multiple layers include, but are not limited to a base layer 106, a packing/absorbent layer 108, and a non-porous adherent top layer 110.

The base layer 106 is in direct contact with the wound bed "w". The base layer 106 is typically porous and non-adherent. "Non-adherent" as used herein refers to a material that does not adhere to tissues in and around the wound bed. "Porous" as used herein refers to a material which contains numerous small perforations or pores which allow wound fluids of all kinds to pass through the material to the dressing layers above. The passage of wound fluid through the porous material is preferably unidirectional such that wound exudate does not flow back to the wound bed. This direction flow feature could be in the form of directional apertures imparted into the material layer, a lamination of materials of different absorption to the base layer 106 or specific material selection that encourages directional flow. Exemplary materials used as the base layer 106 include a contact layer sold under the trademark XEROFLO® by Kendall Corp, a division of TycoHealthcare.

In addition, agents such as hydrogels and medicaments could be bonded or coated to the base layer 106 to reduce bioburden in the wound, promote healing and reduce pain associated with dressing changes or removal. Medicaments include, for example, antimicrobial agents, growth factors, antibiotics, analgesics, and the like. Furthermore, when an analgesic is used, the analgesic could include a mechanism that would allow the release of that agent prior to dressing removal or change.

The layer proximal to the base layer 106 is the packing/absorbent layer 108. The packing/absorbent layer 108 is intended to absorb and capture wound fluid and exudates. Exemplary materials used as the packing/absorbent layer 108 include the antimicrobial dressing sold under the trademark KERLIX® by Kendall Corp., a division of TycoHealthcare. Those skilled in the art will recognize that the packing/absorbent layer 108 can be formed into any suitable shape. The only requirement as to shape is that the packing/absorbent layer 108 is suitable to conform to a particular shape of the wound.

A further use for the packing/absorbent layer 108 is to decrease the incidence of infection in the wound bed. Hence, the packing/absorbent layer 108 may be treated with medicaments. Medicaments include, for example, an anti-infective agent such as an antiseptic or other suitable antimicrobial or combination of antimicrobials, polyhexamethylene biguanide (hereinafter, "PHMB"), antibiotics, analgesics, healing factors such as vitamins, growth factors, nutrients and the like, as well as a simple flushing with isotonic saline solution.

With continued reference still to FIG. 1, the top layer 110 encompasses the perimeter of the wound dressing 102 to surround the wound bed "w" to provide an occlusive seal around the perimeter of the wound bed "w". The top layer 110 may include an adhesive bonded to an area that surrounds the wound bed "w" or may incorporate an additional layer which has the adhesive. The adhesive must provide acceptable adhesion to the tissue "t" surrounding the wound bed "w" skin, e.g., the periwound area, and be acceptable for use on skin without contact deterioration (for example, the adhesive should preferably be non-irritating and non-sensitizing.) The adhesive may be semi-permeable to permit the contacted skin to breathe and transmit moisture. Alternatively, the adhesive may be impermeable. Additionally, the adhesive could be activated or de-activated by an external stimulus such as heat or a given fluid solution or chemical reaction. Adhesives include, for example, the ULTEC Hydrocolloid Dressing, by Kendall Corp., a division of TycoHealthcare.

The top layer 110 is preferably in the form of a sheet mounted proximal to the packing/absorbent layer 108. In a preferred embodiment, the peripheral portions 110P of the top layer 110 includes an adhesive and is secured to the tissue "t" about the wound bed "w". The peripheral portions 110P may be secured to the periphery of base layer 102 if desired. It is anticipated that removable liners may also be used to protect the adhesive surface of the top layer 110 prior to use.

The top layer 110 may incorporate a flexible material, e.g., resilient or elastomeric, that seals the top of the wound dressing 102. In one embodiment, the top layer 110 includes the transparent dressing manufactured under the trademark Polyskin II® by Kendall Corp, a division of TycoHealthcare. POLYSKIN® II is a transparent, semi-permeable material which permits moisture and oxygen exchange with the wound site, and provides a barrier to microbes and fluid containment. In the alternative, the top layer 110 may be impermeable. The transparency of the top layer 110 provides a visual indication of the status of the wound dressing and more particularly, the status of the saturation level of the layers of the wound dressing. The top layer 110 further includes a vacuum port or connector 112 in fluid communication with the interior of the wound dressing 102. The vacuum port 112 may be a separate component attached to the top layer 110 and connected thereto by conventional means or integrally formed with the top layer 110. The vacuum port 112 may have a valve built therein, e.g., a one way valve, to permit exudates to flow in one direction only, i.e., away from the wound dressing 102 toward the pump system 104. Vacuum port 112 is adapted to be releasably connected to the pump system 104 as will be discussed and may or may not include structure for releasable connection to the pump system.

Referring still to FIG. 1, the pump system 104 will be discussed. The pump system 104 includes a vacuum source 114, inlet tubing 116 connecting the inlet side of the vacuum source 114 to the vacuum port 112 of the wound dressing 102 and a collector canister 118 connected to the outlet side of the vacuum source 114 by outlet tubing 120. In the alternative, the collection canister 118 may be disposed "in-line" between the vacuum source 114 and the wound dressing 102. Vacuum source 114 may be any type of pump that is biocompatible and maintains or draws adequate and therapeutic vacuum levels. Preferably, the vacuum level to be achieved is in a range between about 20 mmHg and about 500 mmHg, more preferably, about 75 mmHg and about 125 mmHg. The pump 114 may be removable, reusable, and/or rechargeable. Typically, the pump 114 is a pump of the diaphragmatic or peristaltic type, or the like, in which the moving part(s) draw exudate out of the wound bed into the wound dressing by creating areas or zones of decreased pressure e.g., vacuum zones with the wound dressing 102. This area of decreased pressure preferably communicates with the wound bed "w" to facilitate removal of the fluids therefrom and into the packing/absorbent layer 108. The pump 114 may be actuated by any means known by those skilled in the art. In a preferred embodiment of the present disclosure, the pump 114 is a peristaltic pump. One suitable peristaltic pump is the Kangaroo PET Enternal Feeding Pump manufactured by Kendall Corp., a division of Tyco-Healthcare. Another suitable peristaltic pump may be the model 101 V/R pmy MK2 manufactured by Watson Marlow LTD of England. Preferably, the peristaltic pump produces subatmospheric pressure ranging from about 20 mmHg to about 500 mmHg. A suitable diaphragm pump includes model NMP 850 KNDC manufactured by KNF Neuberger of Germany.

The inlet and outlet tubings 116,120 may be any suitable flexible tubing fabricated from elastomeric and/or polymeric materials. The inlet tubing 116 is preferably releasably connected to the vacuum port 112 through conventional means including a friction fit, bayonet coupling, snap fit or the like. The collection canister 118 may be any flexible disposable pouch or the like. The collection canister 118 may include a super absorbent material such as superabsorbent polymers (SAP), silica gel, sodium polyacrylate, potassium polyacrylamide and related compounds to consolidate or contain wound drainage or debris. The collection canister 118 is preferably transparent to permit viewing into the interior of the canister 118 to assist the patient in determining the remaining capacity of the collection canister 118 and quality of exudates.

Figure 1A:
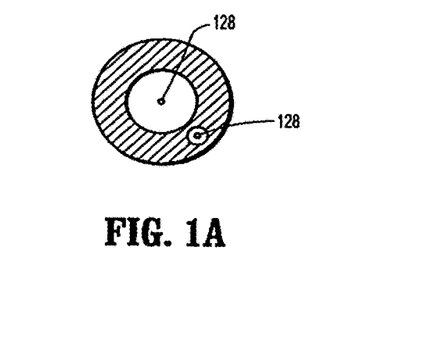
FIG. 1A is a cross-sectional view taken along the lines 1A-1A of FIG. 1 illustrating the vacuum tube of the wound dressing apparatus.
Figure 2:
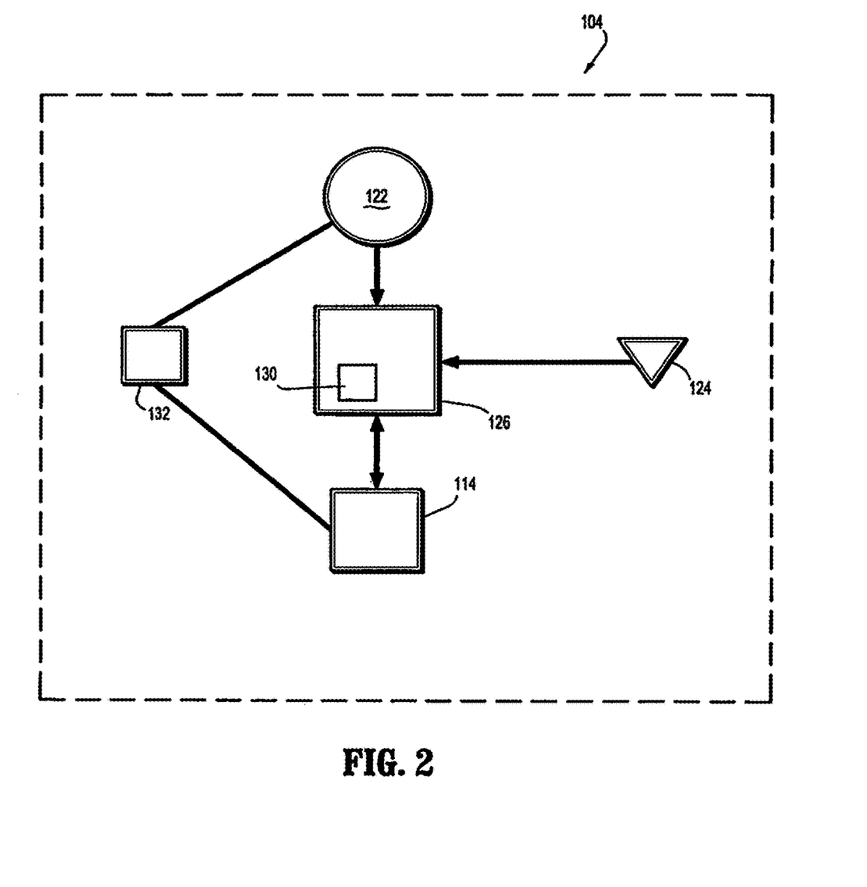
FIG. 2 is a schematic view of the pump system.

Referring to FIG. 2, the pump system 104 preferably includes an internal self contained battery source 122, a pressure sensor or transducer 124 to monitor pressure within the wound dressing, and self-contained regulation or control means 126. The pressure sensor 124 is preferably disposed within the interior of the wound dressing 102 and is in electrical connection with the control means 126 through an electrical wiring 128. (FIG. 1) One suitable pressure sensor is the Dynamic ICP Pressure Sensor of the Pressure Division of PCB Piezotronics, Inc. The pressure sensor 124 would also provide information to assist in detecting a leak in the wound dressing 102. The electrical wiring 128 may be passed through the vacuum port 112 and through inlet tubing 116 or on the exterior surface of the inlet tubing 116. Alternatively, the electrical wiring 128 may pass through a conduit or channel in the wall of the vacuum port 112 and/or the inlet tubing 116. FIG. 1A illustrates the various arrangements where the electrical wiring 128 passes through the channel of the tubing 116 or the central lumen of the tubing 116. The control means 126 is preferably incorporated within the pump housing of the pump 114. The control means 126 may incorporate a motor controller/driver 130 including processing and drive software or circuitry to control or vary the drive voltage to the motor of the pump 114 responsive to the pressure sensed by the pressure sensor 124 and/or other operational parameters including operational time constraints etc. For example, the motor controller/driver may be programmed to run only for a predetermined period of time after start-up. The output of the motor of the pump 114 may be increased or decreased, or initiated or discontinued, as controlled by the control means 126. The regulation or control means 126 may also have an alarm such as a visual, audio or tactile sensory alarm (e.g., vibratory etc.) to indicate to the patient when specific conditions have been met (e.g., the desired vacuum level, loss of vacuum or leak). An override switch 130 may also be incorporated within the pump system to permit the patient to optionally initiate or terminate operation of the pump as desired without input from the control means 126. Wireless means are also envisioned to operate the pump 114 through the control means 126.

Figure 3:
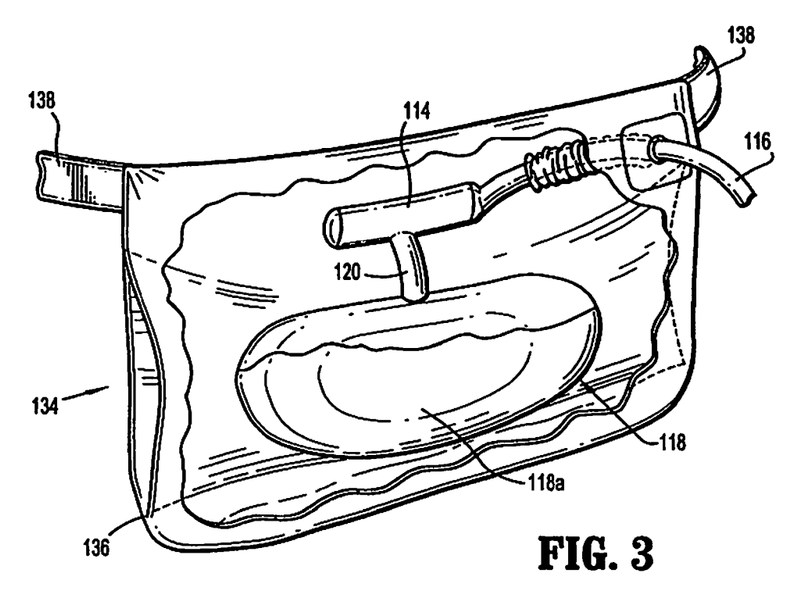
FIG. 3 is a view illustrating a body support bag for containing the collection canister and/or pump system.

With reference now to FIG. 3, there is illustrated a body support bag 134 for supporting at least the canister and/or the pump 114. As discussed, the pump system 104 is adapted for mounting to the body of the patient to be a self contained portal unit. In this regard, the pump system 104 may be at least partially carried or supported by the body support bag 134. The body support bag 134 generally includes a pouch 136 and at least one strap 138, preferably two straps, for securing the pouch 136 to the body of the patient. The body support bag 134 is intended to receive and store at least the collection canister 118 and/or the pump 114. The body support bag 134 may be worn about the waist of the patient. This is desirable in that it may reduce the length of tubing needed depending on the location of the wound. In addition, the pouch 136 may be located adjacent the abdomen of the patient which may present a significantly enhanced ability to conceal the system. The inlet and outlet tubings 116,120 may be secured to the body with tape or the like, or, optionally, may be unsecured and disposed beneath the patient's clothing. Thus, the body support bag 134 permits the patient to move without restrictions or limitations, and provides an entirely portable capability to the patient during wound drainage and healing.

Figure 4:
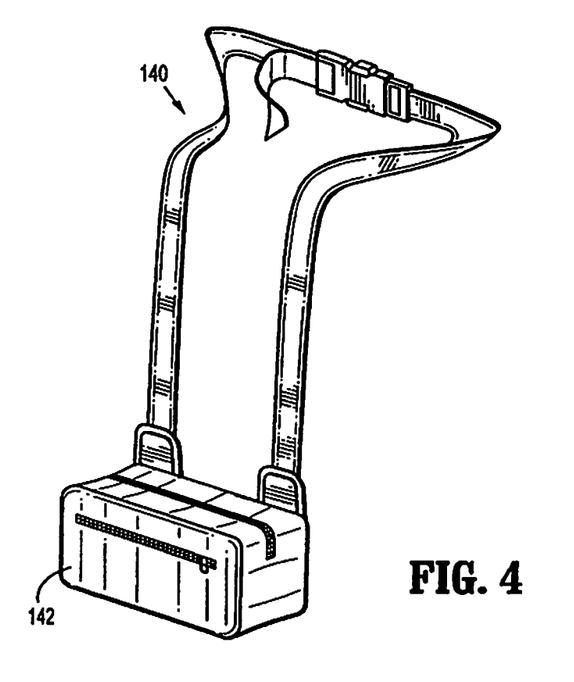
FIG. 4 is a view illustrating an alternate embodiment of the body support bag of FIG. 3.

FIG. 4 illustrates an alternate embodiment of the body support bag. In accordance with this embodiment, the body support bag 140 is adapted for mounting to the shoulder of the patient and has a pouch 142. In other respects, the body support bag 140 functions in a similar manner to the body support bag of FIG. 3.

In use, the wound dressing apparatus 100 is positioned within the wound bed "w" as shown in FIG. 1 and secured about the wound "w" in the manner discussed hereinabove. The pump 114 and/or collection canister 118 are positioned within the pouch 136 of the body support bag 134 (or support bag 140). The body support bag 134, 140 is mounted to the patient either about the waist, shoulder, leg, etc. . . . with the straps 134. The inlet and outlet tubings 114,120 may be secured to the patient's body with tape or the like. Thereafter, the pump 114 is initiated to create a zone of subatmospheric pressure (i.e., a state of vacuum) within the wound dressing 100. The pump 114 may be initiated via the manual override switch 130, or may be started via the pressure sensor 124 which detects the lack of subatmospheric pressure within the wound dressing apparatus 100 and sends a corresponding signal to the control means 126. The control means 126, in turn, activates the pump 114. As the subatmospheric pressure within the wound dressing 102 increases, the top layer 110 and packing/absorbent layer 108 may collapse. Fluids are drawn away from the wound bed "w" and into the packing/absorbent layer 106 of the wound dressing 102. These fluids and/or exudates may be removed from the packing/absorbent layer 106 under the negative pumping energy of the pump 114. The fluids are delivered through the inlet and outlet tubings 116,120 to be collected within the collection canister 118. Once the desired level of subatmospheric pressure is achieved as detected by, e.g., the pressure sensor 124, the pressure sensor 124 sends a signal to the control means 126. The control means 126 may either terminate operation of the pump 114 or alternatively vary the speed or output (e.g., decrease) of the pump 114. In this vacuum state, wound fluid and exudates are continually drawn into the packing/absorbent layer 106. After a period of time, the wound dressing 102 may lose its vacuum state as detected by the pressure sensor 124 or detected visually by the patient. When the loss of a desired vacuum level is achieved, the pressure sensor 124 sends a signal to the control means 126 to activate or increase the output of the pump 114. The pump 114 removes the fluid from the packing/absorbent layer 108 and reestablishes the vacuum state within the wound dressing 102. As indicated hereinabove, in the alternative, the pump 114 may be initiated via the manual override switch 130 when e.g., the patient sees that the collection canister 118 is full. This process may continue several times during wound healing during one application or a series of applications.

Once the wound is fully healed, the wound closure apparatus and pump system may be disposed. The body support bag may also be disposed or cleaned for subsequent use. The pump may be sterilized and reused as well.

Figure 5:
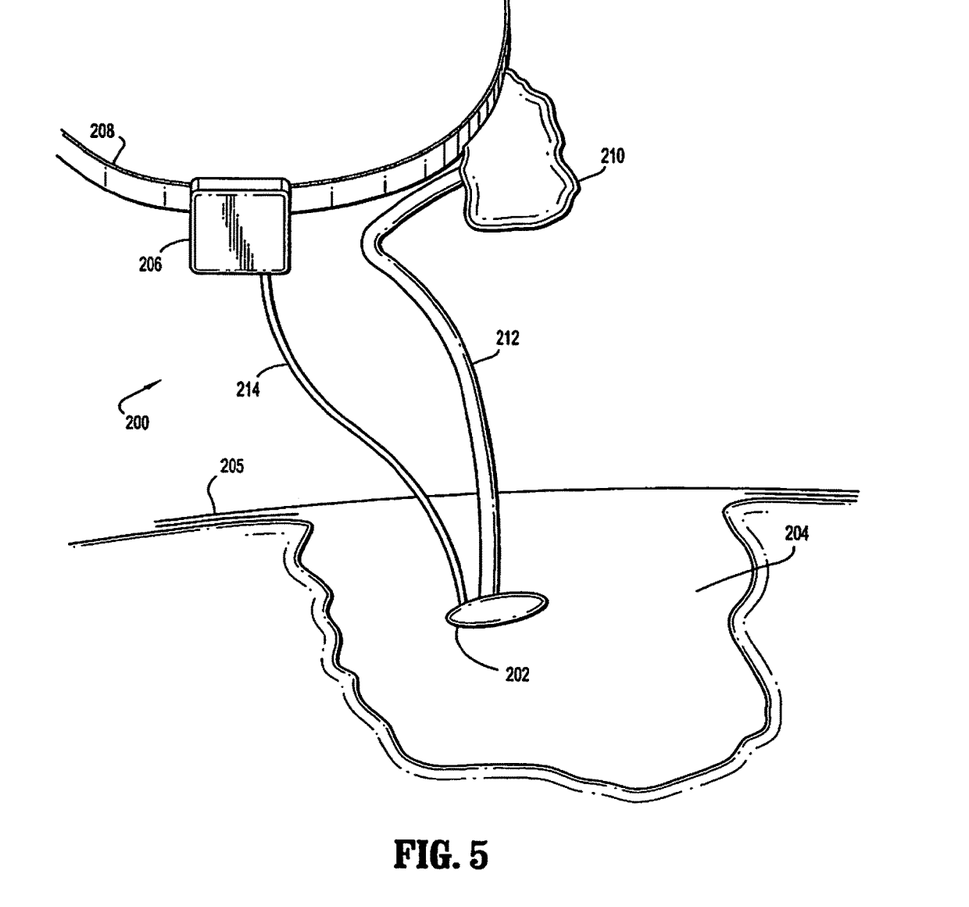
FIG. 5 is a view illustrating an alternate embodiment of the self contained wound dressing apparatus.

FIG. 5 illustrates another embodiment of the present disclosure. In accordance with this embodiment, wound dressing apparatus 200 includes micropump 202 which is adapted for mounting within absorbent layer 204. Micropump 202 has a length ranging from about 1 to 3 inches and a relatively small diameter, preferably, no greater than about one inch. The micropump 202 may be any type of pump that is biocompatible and maintains or draws adequate and therapeutic vacuum levels. The micropump 202 may be removable, reusable, and/or rechargeable. The micropump 202 may be a pump of the diaphragmatic, peristaltic or rotary type, or the like, in which the moving part(s) draw exudates out of the wound bed into the wound dressing by creating areas or zones of decreased pressure e.g., vacuum zones with the wound dressing apparatus 200. This area of decreased pressure preferably communicates with the wound bed "w" to facilitate removal of the fluids therefrom and into the absorbent layer 204. The micropump 202 may be actuated by any means known by those skilled in the art. In a preferred embodiment of the present disclosure, the micropump 202 is a peristaltic pump. One suitable micropump is manufactured by Piab Vacuum Products in Hingham, Mass. Preferably, the peristaltic pump produces subatmospheric pressure ranging from about 20 mmHg to about 500 mmHg.

Absorbent layer 204 is preferably a foam filled dressing which is transparent. The foam may be a resilient, liquid absorbent, porous, polymer-based foam. The foam may be a dispensable liquid which at least partially solidifies to a crystal-like arrangement defining hollow tubes to allow exudates drainage. The foam is dispensed within the wound bed and is potentially collapsible to expel air from the foam channels. The foam may be an expandable hydrophilic foam which is capable of absorbing fluid from a wound and maintain the wound bed moist. The hollow tubes or voids defined by the foam also provide a means to conduct electricity, heat, cold, and ultrasound. The hollow tubes or voids also provide a bioactive scaffold for tissue growth. A thin film transparent top layer 205 is secured about the wound area to enclose the wound.

The self contained battery source and control circuitry may be mounted within housing 206 which is connected to belt 208. Belt 208 is adapted for mounting to the body of a patient, e.g., around the waist area and may include VELCRO® means for securing about the patient. Belt 208 may further support canister 210 which receives the fluid exudates from pump 202 through tube 212. Tube 214 extends from housing 206 to pump 202 and may incorporate electronic wires etc. for operating the pump. In the alternative, tube 212 may incorporate the electrical wires within, e.g., a lumen, and extend from the housing to pump 202 and canister 210.

It is further contemplated that the wound dressing apparatus may incorporate external means or applications to stimulate tissue growth and/or healing. For example, an auxiliary treatment apparatus may be incorporated into the wound dressing apparatus to impart electrical or mechanical energy for the treatment of the tissue such as, for instance, directing electrical, thermal or vibratory energy on the wound area and/or introducing various drugs into the human body through the skin. The auxiliary treatment apparatus may be incorporated into the housing of the pump 202 as shown schematically as reference numeral 216 and operated via a control means discussed hereinabove. One suitable auxiliary treatment apparatus may include an ultrasonic transducer. Other sensor types are also contemplated for incorporation into the wound dressing apparatus including oxygen, chemical, microbial and/or temperature sensors. The detection of oxygen adjacent the wound area would assist the clinician in determining the status of wound healing. The presence of an elevated temperature may be indicative of an infection. The pump system may incorporate circuitry to communicate with a computer, e.g., a hand-held PALM® device through wireless means.

While the disclosure has been illustrated and described, it is not intended to be limited to the details shown, since various modifications and substitutions can be made without departing in any way from the spirit of the present disclosure. For example, it is envisioned that the subject matter of the commonly assigned U.S. patent application Ser. No. 11/517,210, filed on Sep. 6, 2006, which claims priority to Provisional Application No. 60/714,812, filed on Sep. 6, 2005, now issued as U.S. Pat. No. 7,569,742 on Aug. 4, 2009, and the subject matter of the commonly assigned U.S. patent application Ser. No. 11/516,925, filed on Sep. 6, 2006, which claims priority to Provisional Application No. 60/714, 805, filed on Sep. 7, 2005, now issued as U.S. Pat. No. 7,699,823 on Apr. 20, 2010 (the entire contents of each application being incorporated herein) may be incorporated into the present disclosure. As such, further modifications and equivalents of the invention herein disclosed can occur to persons skilled in the art using no more than routine experimentation, and all such modifications and equivalents are believed to be within the spirit and scope of the disclosure as defined by the following claims.

What is claimed is:

1. A negative pressure wound therapy apparatus comprising:
   a wound dressing configured to enclose a wound and provide a seal around a perimeter of the wound, the wound dressing comprising a first layer and a second layer arranged in superposed relation, the first layer configured to absorb and capture wound fluid and the second layer positioned over the first layer;

a pump system comprising:

a vacuum pump configured to apply vacuum pressure to the wound to draw wound fluid away from the wound, wherein the vacuum pump is positioned within the wound dressing;

a pressure sensor configured to detect pressure within the wound dressing, the pressure sensor positioned within the wound dressing;

a controller configured to control the vacuum pump, wherein the pump system is configured to communicate wirelessly with an external electronic device.

2. The apparatus of claim 1, wherein the controller is configured to wirelessly communicate with an external computer.

3. The apparatus of claim 1, wherein the controller is configured to control the vacuum pump in response to a pressure sensed by the pressure sensor.

4. The apparatus of claim 1, wherein the wound dressing further comprises a wound contact layer configured to be in direct contact with the wound.

5. The apparatus of claim 4, wherein the wound contact layer includes a plurality of pores configured to allow unidirectional flow of the wound fluid toward the first layer when vacuum pressure is applied to the wound.

6. The apparatus of claim 4, wherein the wound contact layer includes medicament coated thereto.

7. The apparatus of claim 1, wherein the controller comprises an override switch configured to initiate or terminate operation of the vacuum pump without input from the pressure sensor.

8. The apparatus of claim 1, wherein the first layer comprises an absorbent material.

9. The apparatus of claim 8, wherein the absorbent material comprises a material selected from the group consisting of foams, nonwoven composite fabrics, cellulosic fabrics, super absorbent polymers, and combinations thereof.

10. The apparatus of claim 8, wherein the absorbent material comprises at least one of a medicament, an anti-infective agent, an antimicrobial, polyhexamethylene biguanide, antibiotics, analgesics, healing factors, vitamins, growth factors and nutrients.

11. The apparatus of claim 1, wherein the second layer comprises a transparent material.

12. The apparatus of claim 11, wherein the transparent material is configured to allow a visual indication of the status of the wound dressing.

13. The apparatus of claim 1, wherein the pump system is configured to communicate to the external electronic device at least one of: establishment of a desired vacuum level, loss of vacuum, or a leak.

14. A method of operating a negative pressure wound therapy apparatus, the method comprising:

by a negative pressure source positioned within a wound dressing, applying negative pressure to a wound covered by the wound dressing that comprises a first layer and a second layer arranged in superposed relation, the first layer configured to absorb and capture wound fluid and the second layer positioned over the first layer;

by a pressure sensor positioned within the wound dressing, detecting pressure within the wound dressing; and wirelessly communicating with an external electronic device.

15. The method of claim 14, further comprising controlling the negative pressure source based the detected pressure.

16. The method of claim 14, further comprising wirelessly communicating to the external electronic device at least one of: establishment of a desired vacuum level, loss of vacuum, or a leak.

* * * * *

UNITED STATES PATENT AND TRADEMARK OFFICE
CERTIFICATE OF CORRECTION

PATENT NO. : 10,384,041 B2  
APPLICATION NO. : 15/484622  
DATED : August 20, 2019  
INVENTOR(S) : Harish A. Patel et al.

Page 1 of 1

It is certified that error appears in the above-identified patent and that said Letters Patent is hereby corrected as shown below:

In the Specification

Column 5, Line 22, change "Enternal" to --Enteral--.

In the Claims

Column 10, Line 30 (approx.), in Claim 15, after "based" insert --on--.

Signed and Sealed this  
Twenty-ninth Day of October, 2019

Andrei Iancu  
*Director of the United States Patent and Trademark Office*